US00PP13901P39

(12) United States Plant Patent
Pieters

(10) Patent No.: US PP13,901 P3
(45) Date of Patent: Jun. 24, 2003

(54) CHRYSANTHEMUM PLANT NAMED 'GEDI ONE SOR'

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 6 days.

(21) Appl. No.: 09/873,958

(22) Filed: Jun. 4, 2001

(65) Prior Publication Data

US 2002/0194662 P1 Dec. 19, 2002

(51) Int. Cl.[7] ..... A01H 5/00
(52) U.S. Cl. ..... Plt./289
(58) Field of Search ..... Plt./289, 287

(56) References Cited

U.S. PATENT DOCUMENTS

PP10,216 P 1/1998 Pieters ..... Plt./290
PP10,463 P 6/1998 Wain ..... Plt./289

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant variety characterized by a large decorative type inflorescence, consistent flowering response to short days, blooming consistently after 49 days of short day length, free branching habit, and consistent natural season flowering habit during the first two weeks of September.

1 Drawing Sheet

LATIN NAME

*Dendranthema morifolium.*

VARIETY

Figure 1:
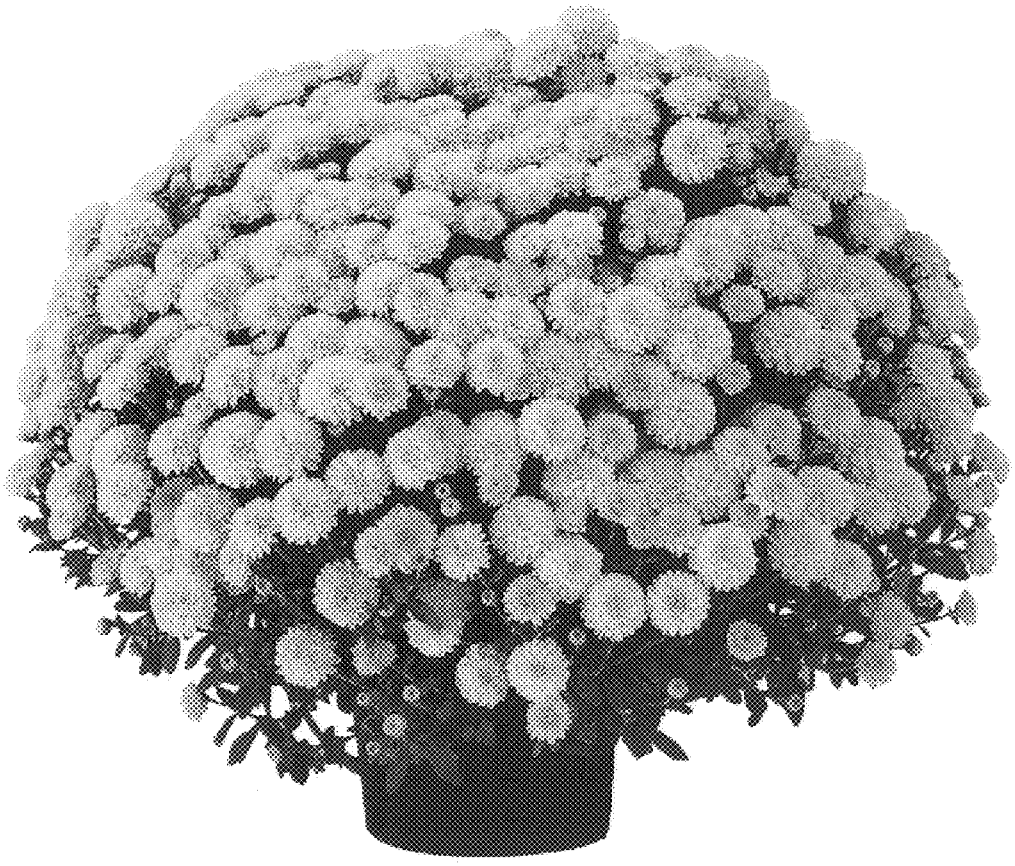

'GEDI ONE SOR'.

BACKGROUND OF THE INVENTION

The present invention relates to a new and distinct cultivar of Chrysanthemum plant, botanically known as *Dendranthema morifolium* and herein after referred to by the cultivar name 'GEDI ONE SOR'.

This new cultivar originated from hybridization of a female parent, cultivar 'Dark Veria' (U.S. Plant Pat. No. 10,215), and a male parent, cultivar 'Orka' (unpatented in the United States). The new cultivar was discovered by the inventor in September 1997.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'GEDI ONE SOR' has not been observed under all possible environmental conditions. The phenotype may vary somewhat with variations in environment such as temperature, daylength, and light intensity, without, however, any variance in genotype.

The following traits have been repeatedly observe and are determined to be the unique characteristics of 'GEDI ONE SOR.' These observations were made on plants approximately 120 days old from rooted cuttings. These characteristics in combination distinguish 'GEDI ONE SOR' as a new and distinct Chrysanthemum:

1. Large decorative type inflorescence;

2. Consistent flowering response to short days, blooming consistently after 49 days of short day length;

3. Free branching habit; and

4. Consistent natural season flowering habit during the first two weeks of September.

Plants of the new cultivar are similar to plants of the parent cultivar, 'Dark Veria,' in most horticultural characteristics, however plants of the new cultivar differed from plants of the cultivar 'Dark Veria' in the following characteristics:

1. The new cultivar has a wider diameter flower;

2. The new cultivar has many more ray florets than the parent;

3. The new cultivar is taller and wider; and

4. The new cultivar naturally blooms 3 weeks earlier.

Plants of the new cultivar are also similar to plants of the parent cultivar, 'Orka,' in most horticultural characteristics, however plants of the new cultivar differed from plants of the cultivar 'Orka' in the following characteristics:

1. The new cultivar has a wider diameter flower;

2. The new cultivar has many more ray florets than the parent; and

3. The new cultivar is taller and wider.

The new cultivar can be compared to the Chrysanthemum cultivar 'CLEAGAR GF1' (disclosed in U.S. Plant Pat. No. 10,463). However plants of the new Chrysanthemum differed from the plants of the cultivar 'CLEAGAR GF1' in the following characteristics:

1. The new cultivar naturally blooms 2 weeks earlier;

2. The new cultivar has larger diameter blooms;

3. The new cultivar has more blooms per flowering branch; and

4. The new cultivar is taller and wider.

BRIEF DESCRIPTION OF THE PHOTOGRAPHS

The photograph shows a plant of 'GEDI ONE SOR' grown in a 2-gallon container. A single cutting was used in the pot, planted mid-May and grown under outdoor field conditions.

DETAILED BOTANICAL DESCRIPTION

In the following description, color references are made to The Royal Horticultural Society Colour Chart except where general terms of ordinary dictionary significance are used. The following observations and measurements describe plants grown in a commercial field in Oxnard, Calif. in the month of September 2000. The growing conditions range from 60° to 65° F. at night to 70° to 85° F. during the day. Measurements and numerical values represent averages of typical flowering types.

Botanical classification: *Dendranthema morifolium* cultivar 'GEDI ONE SOR'.
Commercial classification: Garden-type Chrysanthemum.
Parentage: Hybridization of female parent 'Dark Veria' (U.S. Plant Pat. No. 10,216) and male parent 'Orka' (unpatented in the United States).

PROPAGATION

Time to rooting: 7 to 14 days at approximately 21° C.
Root description: Fine, fibrous.

PLANT

Growth habit: Mounding herbaceous perennial.
Height: Approximately 27 cm.
Plant spread: Approximately 29 cm.
Growth rate: Moderate.
Branching characteristics: Free Branching.
Internode length: Approximately 2.8 cm.
Length of lateral branches: Approximately 21 cm.
Number of leaves per lateral branch: Approximately 22.
Stem color: Near 138A.

FOLIAGE

Leaf:
- *Arrangement.*—Alternate, single.
- *Average length.*—Approximately 6.2 cm.
- *Average width.*—Approximately 3.0 cm.
- *Shape of blade.*—Ovate.
- *Apex.*—Acuminate.
- *Base.*—Attenuate.
- *Attachment.*—Stalked.
- *Margin.*—Pinnately lobed and toothed.
- *Texture of top surface.*—Lightly pubescent.
- *Texture of bottom surface.*—Lightly pubescent.
- *Color.*—Young foliage upper side: Near 137A. Young foliage under side: Near 137B. Mature foliage upper side: Near 137A. Mature foliage under side: Near 137B. Venation upper side: Near 138C. Venation under side: Near 137C.

Petiole:
- *Average length.*—Approximately 2.1 cm.
- *Color.*—Near 137B.
- *Diameter.*—Approximately 0.3 cm.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately the first two weeks of September.
- *Number of inflorescences per stem.*—Approximately 16.
- *Inflorescence diameter.*—Approximately 5.5 cm.
- *Inflorescence depth.*—2.5 cm.
- *Inflorescence longevity on plant.*—Approximately 25–29 days.
- *Persistence.*—Persistent.

Ray florets:
- *Appearance.*—Matte.
- *Texture.*—Smooth.
- *Average number per flower.*—300.
- *Shape.*—Oblanceolate.
- *Margin.*—Entire.
- *Apex.*—Obtuse.
- *Length.*—Approximately 3.1 cm.
- *Width.*—Approximately 0.8 cm.
- *Color.*—Upper surface at first opening: Near 13B. Upper surface at maturity: Near 13B. Upper surface at fading: Near 13C. Under surface at first opening: Near 13B. Under surface at maturity: Near 13B. Under surface at fading: Near 13C.

Disc florets:
- *Appearance.*—Shiny.
- *Texture.*—Smooth.
- *Average number per flower.*—Approximately 20.
- *Shape.*—Cylindric.
- *Apex.*—Obtuse.
- *Average length.*—Approximately 1.0 cm.
- *Average width.*—Approximately 0.2 cm.
- *Color.*—At first opening: Near 2A. At maturity: Near 7A. At fading: Near 16A.

Peduncle:
- *Length.*—At terminal end (shortest): Approximately 5 cm. At lateral end (longest): Approximately 11 cm.
- *Diameter.*—Approximately 0.4 cm.
- *Strength.*—Moderate.
- *Color.*—Near 137C.
- *Habit.*—Erect.
- *Surface texture.*—Lightly pubescent.

Inflorescence bud:
- *Length.*—Approximately 1.0 cm.
- *Diameter.*—Approximately 1.0 cm.
- *Form.*—Globular.
- *Color.*—Near 13A.

Phyllaries:
- *Appearance.*—Matte.
- *Texture.*—Lightly pubescent.
- *Number.*—Approximately 20 to 30.
- *Shape.*—Ovate.
- *Margin.*—Entire.
- *Apex.*—Acute.
- *Diameter.*—Approximately 0.3 cm.
- *Length.*—Approximately 0.4 cm.
- *Color.*—Upper side: Near 138A. Under side: Near 138A.

REPRODUCTIVE ORGANS

Ray florets:
- *Number of pistils per flower.*—1.
- *Stigma shape.*—2 branched.

*Stigma color.*—Near 13B.
*Style color.*—Near 13D.
*Style length.*—Approximately 0.6 cm.
*Stamens.*—Not present.

Disc florets:

*Number of pistils per flower.*—1.
*Stigma shape.*—Cylindric.
*Style length.*—Approximately 0.5 cm.
*Number of stamens per flower.*—Approximately 5.
*Anther shape.*—Tubular.
*Anther color.*—Near 14C.
*Pollen color.*—Near 14B.

OTHER CHARACTERISTICS

Seed production: Commercially, this plant is not used or observed in a stage wherein seeds would be produced. Therefore, seed production has not been observed.

Flower fragrance: Absent.

Disease resistance: Neither resistance nor susceptibility to diseases and pests have been observed in this cultivar.

What is claimed is:

1. A new and distinct variety of Chrysanthemum plant named 'GEDI ONE SOR' as herein illustrated and described.

* * * * *